US011288804B2

(12) United States Patent
Wang et al.

(10) Patent No.: US 11,288,804 B2
(45) Date of Patent: Mar. 29, 2022

(54) BRAIN TUMOR IMAGE SEGMENTATION METHOD, DEVICE AND STORAGE MEDIUM

(71) Applicants: Siemens Healthcare GmbH, Erlangen (DE); Henan Provincial People's Hospital, Zhengzhou (CN)

(72) Inventors: Mei Yun Wang, Zhengzhou (CN); Yan Bai, Zhengzhou (CN); Tian Yi Qian, Beijing (CN); Jing Zhou, Zhengzhou (CN); Wei Wei, Zhengzhou (CN)

(73) Assignee: Siemens Healthcare GmbH, Erlangen (DE)

( * ) Notice: Subject to any disclaimer, the term of this patent is extended or adjusted under 35 U.S.C. 154(b) by 277 days.

(21) Appl. No.: 16/722,751

(22) Filed: Dec. 20, 2019

(65) Prior Publication Data
US 2020/0202532 A1  Jun. 25, 2020

(30) Foreign Application Priority Data
Dec. 20, 2018 (CN) .......................... 201811577618.9

(51) Int. Cl.
*G06K 9/00* (2006.01)
*G06T 7/00* (2017.01)
(Continued)

(52) U.S. Cl.
CPC .......... *G06T 7/0016* (2013.01); *A61B 5/0042* (2013.01); *A61B 5/055* (2013.01);
(Continued)

(58) Field of Classification Search
CPC .................................................. G06T 7/0016
See application file for complete search history.

(56) References Cited

U.S. PATENT DOCUMENTS

| 2013/0223714 A1* | 8/2013 | Lipton | .................. G06T 7/0014 382/131 |
| 2015/0080703 A1* | 3/2015 | Reiman | ................ A61B 5/0035 600/409 |
| 2016/0343127 A1* | 11/2016 | Miller | .................... A61B 5/055 |

OTHER PUBLICATIONS

Wu, Chen-Xing et al. "Peritumoral edema on magnetic resonance imaging predicts a poor clinical outcome in malignant glioma" Oncology Letters, vol. 10, pp. 2769-2776, Nov. 2015 // DOI: 10.3892/ol.2015.3639.

(Continued)

*Primary Examiner* — Oneal R Mistry
(74) *Attorney, Agent, or Firm* — Schiff Hardin LLP

(57) ABSTRACT

A brain tumor image segmentation method and device are disclosed. The disclosed method includes acquiring a basic white matter template generated based on brain magnetic resonance images of a plurality of healthy samples, collecting corresponding low, mid and high b-value diffusion weighted images of the brain of a patient, segmenting out a tumor region including the tumor body and the edema on each image based on the signal distribution of each image in a first set image group of the patient, removing the normal white matter region from the tumor region according to the basic white matter template and the high b-value diffusion weighted image, and classifying the value of the voxel in each image in a second set image group and a second apparent diffusion coefficient image obtained through calculations to obtain a tumor body region and an edema region.

15 Claims, 7 Drawing Sheets

(51) Int. Cl.
*A61B 5/00* (2006.01)
*G01R 33/56* (2006.01)
*G06T 7/11* (2017.01)
*G06T 7/155* (2017.01)
*G06T 7/30* (2017.01)
*A61B 5/055* (2006.01)

(52) U.S. Cl.
CPC .......... *A61B 5/4878* (2013.01); *A61B 5/7246* (2013.01); *A61B 5/7253* (2013.01); *G01R 33/5602* (2013.01); *G06T 7/11* (2017.01); *G06T 7/155* (2017.01); *G06T 7/30* (2017.01); *G06T 2207/10088* (2013.01); *G06T 2207/20036* (2013.01); *G06T 2207/20076* (2013.01); *G06T 2207/30016* (2013.01); *G06T 2207/30096* (2013.01)

(56) References Cited

OTHER PUBLICATIONS

Dhermain, Frederic G. et al. "Advanced MRI and PET imaging for assessment of treatment response in patients with gliomas" The Lancet Neurology, vol. 9, No. 9, pp. 906-920, Sep. 1, 2010 (Published online: Aug. 11, 2010) // DOI:https://doi.org/10.1016/S1474-4422(10)70181-2.

Senft, Christian et al. "Intraoperative MRI guidance and extent of resection in glioma surgery: a randomised, controlled trial" The Lancet Oncology, vol. 12, No. 11, pp. 997-1003, Oct. 1, 2011 (Published Online Aug. 24, 2011) // DOI: https://doi.org/10.1016/S1470-2045(11)70196-6.

* cited by examiner

BRAIN TUMOR IMAGE SEGMENTATION METHOD, DEVICE AND STORAGE MEDIUM

CROSS-REFERENCE TO RELATED APPLICATIONS

The present application claims the benefit of the filing date of China patent application no. 201811577618.9, filed on Dec. 20, 2018, the contents of which are incorporated herein by reference in their entirety.

TECHNICAL FIELD

The present disclosure relates to the magnetic resonance imaging system and, in particular, to a brain tumor image segmentation method, device, and storage medium.

BACKGROUND

Brain tumors are one of the major diseases that severely jeopardize the health of human beings. Neuroglioma is a type of malignant brain tumors with a high fatality rate. Since a brain tumor is a space-occupying lesion, edemas often occur to the tissues around the brain tumor. Edemas are mainly caused by the penetrating fluid of the tumor and include vasogenic edemas. The tumor resection, the edema scope, and the edema shape are closely related to the prognostic effect of a patient. If the tumor is resected more completely, the prognostic effect of the patient is better, and the patient may survive longer. Therefore, the accurate identification of the tumor boundary plays a key role in the complete resection of the tumor. In addition, a large edema region indicates a poor prognostic effect of the patient, and an irregular edema has a poorer prognostic effect than a regular edema does. Therefore, the accurate determination of the edema region and the edema shape can help improve the accuracy rate of the prognosis.

Magnetic resonance imaging (MRI), the most common brain tumor examination and diagnostic means, is used to segment a brain tumor out of a magnetic resonance image. However, current brain tumor segmentation is only limited to the separation of a tumor region including a tumor body and an edema from normal brain tissues, and cannot clearly determine the boundary between the tumor body and the edema.

SUMMARY

The embodiments of the present disclosure provide a brain tumor image segmentation method in one aspect, and provide a brain tumor image segmentation device and a computer-readable storage medium in another aspect to separate the tumor body region from the edema region in a tumor region.

A brain tumor image segmentation method provided in the embodiments of the present disclosure comprises: acquiring a basic white matter template generated based on brain magnetic resonance images of a plurality of healthy samples; collecting a morphological image of the 3-D standard brain template of the head of a patient and corresponding low, mid, and high b-value diffusion weighted images; registering the basic white matter template with the morphological image of the 3-D standard brain template of the patient to obtain an individual white matter template; segmenting out the tumor region including the tumor body and the edema on each image of the patient based on the signal distribution of each image in a first set image group of the patient; comparing the high b-value diffusion weighted image with the individual white matter template to obtain a mask configured to indicate a normal white matter region; removing the normal white matter region from the tumor region according to the mask; for each voxel in the tumor region from which the normal white matter region is removed, classifying the value of the voxel in each image in a second set image group as an eigenvector, and segmenting the image to obtain a tumor body region and an edema region, wherein the second set image group includes the high b-value diffusion weighted image, the first apparent diffusion coefficient image obtained through calculations according to the low and mid b-value diffusion weighted images of the patient and the second apparent diffusion coefficient image obtained through calculations according to the mid and high b-value diffusion weighted images of the patient.

In one embodiment, acquiring a basic white matter template generated based on brain magnetic resonance images of a plurality of healthy samples comprises: collecting morphological images of the 3-D standard brain templates of the heads of a plurality of healthy samples and corresponding low, mid, and high b-value diffusion weighted images; for each healthy sample, registering the low, mid and high b-value diffusion weighted images of the healthy sample with the morphological image of the 3-D standard brain template of the healthy sample to obtain the healthy sample's low, mid, and high b-value diffusion weighted images with the standard space and resolution; performing a standard brain template space transformation for the morphological image of the 3-D standard brain template of each healthy sample of the plurality of healthy samples to obtain a transformation matrix of each healthy sample from the individual space to the standard space; for each healthy sample, applying the transformation matrix of the healthy sample to the high b-value diffusion weighted image of the healthy sample in the standard space and resolution condition to obtain the projection of the high b-value diffusion weighted image of each healthy sample in the standard space; generating statistics of the projections of the high b-value diffusion weighted images of the plurality of healthy samples in the standard space to obtain a fiber bundle probability distribution graph of overall samples and using the fiber bundle probability distribution graph as a basic white matter template.

In one embodiment, the first set image group includes the first apparent diffusion coefficient image and the second apparent diffusion coefficient image, and segmenting out the tumor region including the tumor body and the edema on each image of the patient based on the signal distribution of each image in the first set image group of the patient comprises: segmenting the first apparent diffusion coefficient image and the second apparent diffusion coefficient image according to the abnormal signal distributions in the two images respectively to obtain the abnormal signal regions and taking the combined set of the two abnormal signal regions to obtain a tumor region including the tumor body and the edema.

In one embodiment, the first set image group includes the low b-value diffusion weighted image, T1 enhanced image, or T2 plain-scan image.

In one embodiment, the method further comprises: classifying the eigenvector constituted by the signal intensity of the voxel in the same position in the tumor body region in a third set image group according to the predetermined tumor cell grading information to obtain the tumor cell grade of the patient.

In one embodiment, the third set image group includes any of the low, mid, and high b-value diffusion weighted images, the first apparent diffusion coefficient image, and the second apparent diffusion coefficient image of the patient, or any combination thereof.

In one embodiment, the low b-value is a b-value equal to 0, the mid b-value is a b-value ranging from 1000 to 4000, and the high b-value is a b-value greater than 5000.

A brain tumor image segmentation device provided in the embodiments of the present disclosure comprises: a template generation module, configured to acquire a basic white matter template generated based on brain magnetic resonance images of a plurality of healthy samples; an image acquisition module, configured to collect a morphological image of the 3-D standard brain template of the head of a patient and corresponding low, mid, and high b-value diffusion weighted images; a template transformation module, configured to register the basic white matter template with the morphological image of the 3-D standard brain template of the patient to obtain an individual white matter template; a first region segmentation module, configured to segment out the tumor region including the tumor body and the edema on each image of the patient based on the signal distribution of each image in a first set image group of the patient; a mask generation module, configured to compare the high b-value diffusion weighted image with the individual white matter template to obtain a mask configured to indicate a normal white matter region; a white matter removal module, configured to remove the normal white matter region from the tumor region according to the mask; a second region segmentation region, configured to classify the value of the voxel in each image in a second set image group as an eigenvector for each voxel in the tumor region from which the normal white matter region is removed and segment the image to obtain a tumor body region and an edema region, wherein the second set image group includes the high b-value diffusion weighted image, the first apparent diffusion coefficient image obtained through calculations according to the low and mid b-value diffusion weighted images of the patient and the second apparent diffusion coefficient image obtained through calculations according to the mid and high b-value diffusion weighted images of the patient.

In one embodiment, the template generation module comprises: an image acquisition unit, configured to collect morphological images of the 3-D standard brain templates of the heads of a plurality of healthy samples and corresponding low, mid, and high b-value diffusion weighted images; a registration unit, configured to register the low, mid and high b-value diffusion weighted images of each healthy sample with the morphological image of the 3-D standard brain template of the healthy sample to obtain the healthy sample's low, mid, and high b-value diffusion weighted images with the standard space and resolution; a space transformation unit, configured to perform a standard brain template space transformation for the morphological image of the 3-D standard brain template of each healthy sample of the plurality of healthy samples to obtain a transformation matrix of each healthy sample from the individual space to the standard space; a weighted image processing unit, configured to apply the transformation matrix of each healthy sample to the high b-value diffusion weighted image of the healthy sample in the standard space and resolution condition to obtain the projection of the high b-value diffusion weighted image of each healthy sample in the standard space; a template determination unit, configured to generate statistics of the projections of the high b-value diffusion weighted images of the plurality of healthy samples in the standard space to obtain a fiber bundle probability distribution graph of overall samples and use the fiber bundle probability distribution graph as a basic white matter template.

In one embodiment, the first set image group includes the first apparent diffusion coefficient image and the second apparent diffusion coefficient image, the first region segmentation module segments the first apparent diffusion coefficient image and the second apparent diffusion coefficient image according to the abnormal signal distributions in the two images, respectively, to obtain the abnormal signal regions and takes the combined set of the two abnormal signal regions to obtain a tumor region including the tumor body and the edema.

In one embodiment, the first set image group includes the low b-value diffusion weighted image, T1 enhanced image, or T2 plain-scan image.

In one embodiment, the device further comprises a grading module configured to classify the eigenvector constituted by the signal intensity of the voxel in the same position in the tumor body region in a third set image group according to the predetermined tumor cell grading information to obtain the tumor cell grade of the patient.

In one embodiment, the third set image group includes any of the low, mid, and high b-value diffusion weighted images, the first apparent diffusion coefficient image, and the second apparent diffusion coefficient image of the patient, or any combination thereof.

In one embodiment, the low b-value is a b-value equal to 0, the mid b-value is a b-value ranging from 1000 to 4000, and the high b-value is a b-value greater than 5000.

Another brain tumor image segment device provided in the embodiments of the present disclosure comprises at least a memory and at least a processor, wherein the at least one memory is configured to store a computer program, and the at least one processor is configured to invoke the computer program stored in the at least one memory to execute the brain tumor image segmentation method in any of the above-mentioned embodiments.

A computer-readable storage medium provided in the embodiments of the present disclosure stores a computer program and the computer program can be executed by a processor to realize the brain tumor image segmentation method in any of the above-mentioned embodiments.

It can be seen from the above-mentioned solution that high b-value diffusion weighted images which can effectively present a white matter region and apparent diffusion coefficient images which are obtained through calculations based on a set high b-value and a set mid b-value and can effectively present a gray matter region and a tumor region are introduced in the embodiments of the present disclosure, the white matter region is removed from the tumor region in the above-mentioned two apparent diffusion coefficient images by acquiring the white matter template generated based on the brain magnetic resonance images of healthy samples, and the tumor body region and the edema region are further segmented out by comparing the image of the tumor region from which the white matter region is removed.

In addition, when the tumor region including the tumor body and the edema is segmented, a plurality of optional solutions are available and the segmentation can be realized flexibly.

Further, a method of setting specific low, mid and high b-values is given.

In addition, the tumor cell grade of a patient is obtained by classifying the eigenvector constituted by the signal intensity of the voxel in the same position in the tumor body region in a third set image group according to the predetermined tumor cell grading information, thus facilitating the subsequent diagnosis and treatment.

BRIEF DESCRIPTION OF THE DRAWINGS/FIGURES

The following will describe in detail the preferred embodiments of the present disclosure by reference to the drawings so that those skilled in the art can have a clearer idea of the above-mentioned and other characteristics and advantages of the present disclosure.

DESCRIPTION OF REFERENCE NUMERALS IN THE DRAWINGS

Figure 1:
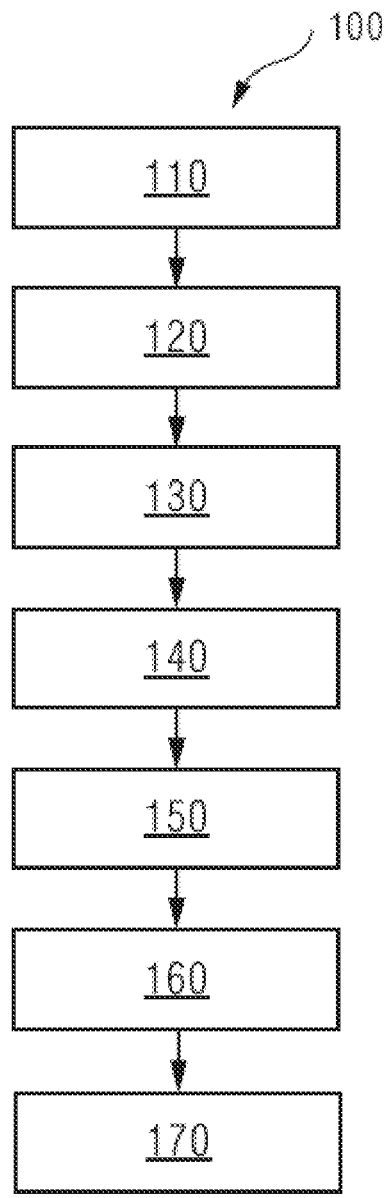
FIG. 1 is an exemplary flowchart of the brain tumor image segmentation method in accordance with embodiments of the present disclosure.

| Reference numeral | Meaning |
| --- | --- |
| 100 | Brain tumor image segmentation method |
| 110-170, 111-115 | Steps |
| 500, 600 | Brain tumor image segmentation device |
| 510 | Template generation module |
| 511 | Image acquisition unit |
| 512 | Registration unit |
| 513 | Space transformation unit |
| 514 | Weighted image processing unit |

-continued

| Reference numeral | Meaning |
| --- | --- |
| 515 | Template determination unit |
| 520 | Image acquisition module |
| 530 | Template transformation module |
| 540 | First region segmentation module |
| 550 | Mask generation module |
| 560 | White matter removal module |
| 570 | Second region segmentation module |
| 580 | Grading module |
| 601 | Memory |
| 602 | Processor |
| 603 | Bus |

DETAILED DESCRIPTION

To further segment the tumor body region and the edema region out of the tumor region, the inventors of the present application, after creative work, finds that the white matter region can be effectively presented in an ultra-high b-value (for example, a b-value greater than 5000, such as b10000) diffusion weighted image (UHB-DWI), that is to say, only the white matter region and tumor cells present high signal intensities in an ultra-high b-value diffusion weighted image. In addition, the application further finds that the gray matter region and the tumor region can be effectively presented in an apparent diffusion coefficient image (ADCU) obtained through calculations by use of the change rate of the voxel in the same position in mid b-value and high b-value diffusion weighted images, and that these two images can both be used to remove water signals from a low b-value (for example, b0) diffusion weighted image or a T2 weighted image (also known as T2 plain-scan image). Therefore, in the embodiments of the present disclosure, the high b-value diffusion weighted image and the apparent diffusion coefficient image obtained through calculations based on a set high b-value and a set mid b-value are introduced, the white matter region is removed from the two images by acquiring the white matter template generated based on brain magnetic resonance images of healthy samples, and the tumor body region and the edema region are further segmented out by comparing the images from which the white matter region is removed.

To make the objectives, technical solutions, and advantages of the present disclosure clearer, the following gives embodiments to further describe the present disclosure in detail.

FIG. 1 is an exemplary flowchart of the brain tumor image segmentation method 100 in the embodiments of the present disclosure. As shown in FIG. 1, the method 100 may comprise the following steps:

Step 110: Acquire a basic white matter template generated based on brain magnetic resonance images of a plurality of healthy samples.

The basic white matter template in this step may be generated in a plurality of ways, and it may be generated previously or may be generated when the brain tumor image segmentation method in the present application is executed. It may be generated in the way shown in FIG. 4 or may be generated in other ways.

Step 120: Collect a morphological image of the 3-D standard brain template of the head of a patient and corresponding low, mid, and high b-value diffusion weighted images.

The corresponding low, mid, and high b-values can be any suitable values that are determined according to the actual application. For example, in one embodiment, the low b-value is a b-value equal to 0, the mid b-value is a b-value ranging from 1000 to 4000, and the high b-value is a b-value greater than 5000.

Figure 2A:
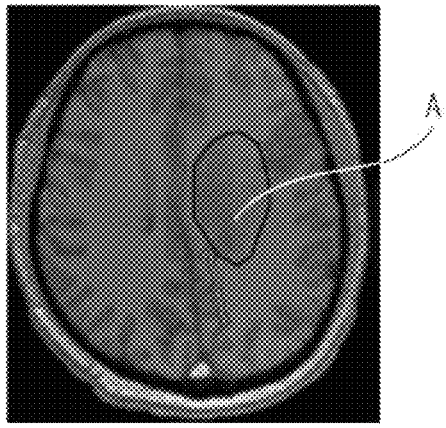
FIGS. 2A to 2D are respectively a morphological image of the 3-D standard brain template of a patient, and the corresponding low, mid and high b-value diffusion weighted images in accordance with an example embodiment of the present disclosure.
Figure 2B:
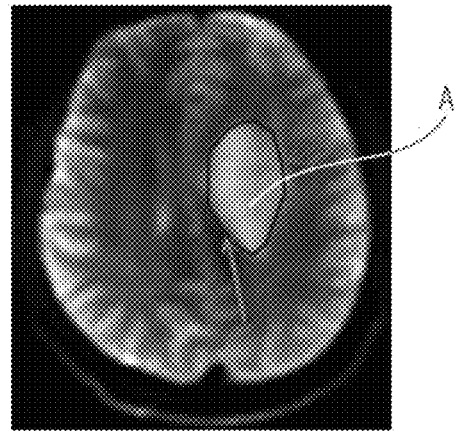
Figure 2C:
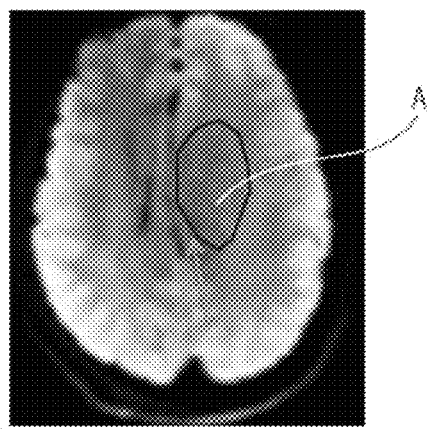
Figure 2D:
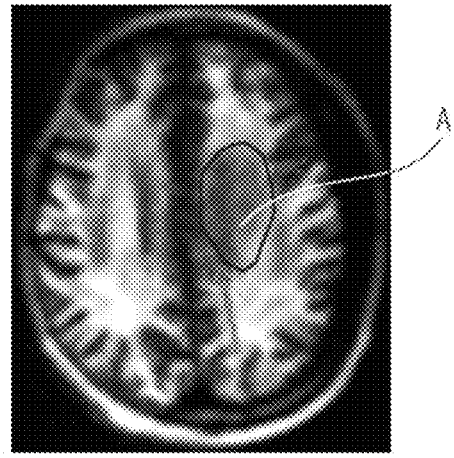

FIGS. 2A to 2D are respectively a morphological image of the 3-D standard brain template of a patient, and the corresponding low, mid, and high b-value diffusion weighted images in an example. FIG. 2A is a morphological image of the 3-D standard brain template of the patient, FIG. 2B is a b0 diffusion weighted image of the patient, FIG. 2C is a b1000 diffusion weighted image of the patient and FIG. 2D is a b10000 diffusion weighted image of the patient.

Step 130: Register the basic white matter template with the morphological image of the 3-D standard brain template of the patient to obtain an individual white matter template.

Step 140: Segment out the tumor region including the tumor body and the edema on each image of the patient based on the signal distribution of each image in a first set image group of the patient.

In this step, a plurality of implementation methods are available. Two examples are listed below.

First Method:

The first set image group includes the low b-value diffusion weighted image, T1 enhanced image, or T2 plain-scan image. Accordingly, the tumor region including the tumor body and the edema can be segmented out on each image of the patient according to the abnormal signal region in the low b-value diffusion weighted image, T1 enhanced image, or T2 plain-scan image in this step.

Abnormal signals in the embodiments of the present disclosure refer to the signals obtained relative to the set normal signal threshold in an image, for example signals exceeding the normal signal threshold in an image.

Generally, a T1 enhanced image is used to observe the blood-brain barrier disruption around the tumor and the malignant degree of the tumor. A T2 plain-scan image is also known as a T2 weighted image. However, both a T1 enhanced image and a T2 plain-scan image are used to observe whether an abnormal tissue exists in a brain.

Second Method:

The apparent diffusion coefficient of the voxel in a position is calculated according to the change rate of the voxel in the same position in low and mid b-value diffusion weighted images of the patient to obtain a first apparent diffusion coefficient image (ADCH) constituted by the apparent diffusion coefficients of the voxels in all positions, and the apparent diffusion coefficient of the voxel in a position is calculated according to the change rate of the voxel in the same position in mid and high b-value diffusion weighted images to obtain a second apparent diffusion coefficient image (ADCU) constituted by the apparent diffusion coefficients of the voxels in all positions.

Figure 2E:
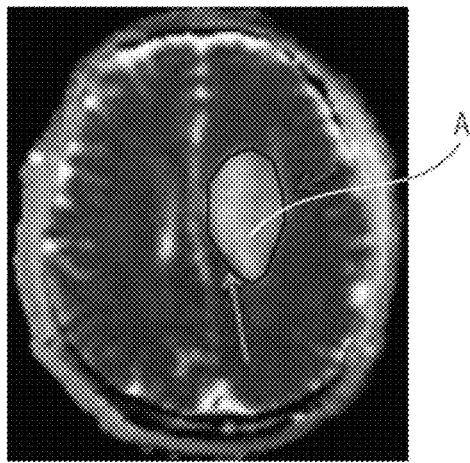
FIG. 2E is a first apparent diffusion coefficient image obtained through calculations based on the diffusion weighted images shown in FIGS. 2B and 2C.
Figure 2F:
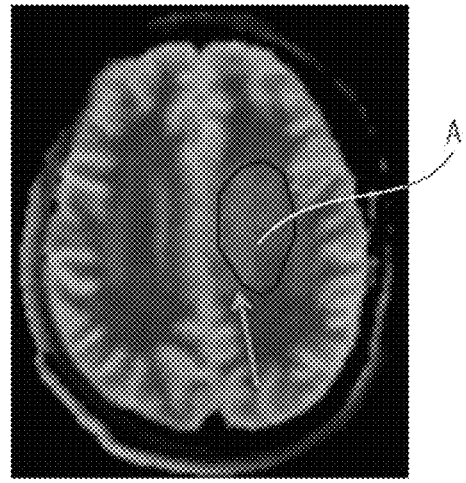
FIG. 2F is a second apparent diffusion coefficient image obtained through calculations based on the diffusion weighted images shown in FIGS. 2C and 2D.

FIG. 2E is a first apparent diffusion coefficient image obtained in one example through calculations based on the diffusion weighted images shown in FIGS. 2B and 2C, and FIG. 2F is a second apparent diffusion coefficient image obtained in one example through calculations based on the diffusion weighted images shown in FIGS. 2C and 2D.

Accordingly, the first set image group includes the first apparent diffusion coefficient image (ADCH) and the second apparent diffusion coefficient image (ADCU). In this step, the abnormal signal regions are respectively segmented out of the first apparent diffusion coefficient image and the second apparent diffusion coefficient image according to the abnormal signal distribution in the two images, and the combined set of the two abnormal signal regions is taken to obtain the tumor region including the tumor body and the edema.

Region A in FIGS. 2A to 2F is the tumor region obtained through segmentations and including the tumor body and the edema.

Step 150: Compare the high b-value diffusion weighted image with the individual white matter template to obtain a mask used to indicate a normal white matter region.

Step 160: Remove the normal white matter region from the tumor region according to the mask.

Step 170: For each voxel in the tumor region from which the normal white matter region is removed, classify the value of the voxel in each image in a second set image group as an eigenvector and segment the image to obtain a tumor body region and an edema region. The second set image group includes the high b-value diffusion weighted image, the first apparent diffusion coefficient image obtained through calculations according to the low and mid b-value diffusion weighted images of the patient and the second apparent diffusion coefficient image obtained through calculations according to the mid and high b-value diffusion weighted images of the patient. In addition, other images may be included, and the images included in the second set image group are by way of example and not limitation.

After the above-mentioned processing, the segmentations of the tumor body region and the edema region are completed.

Figure 2G:
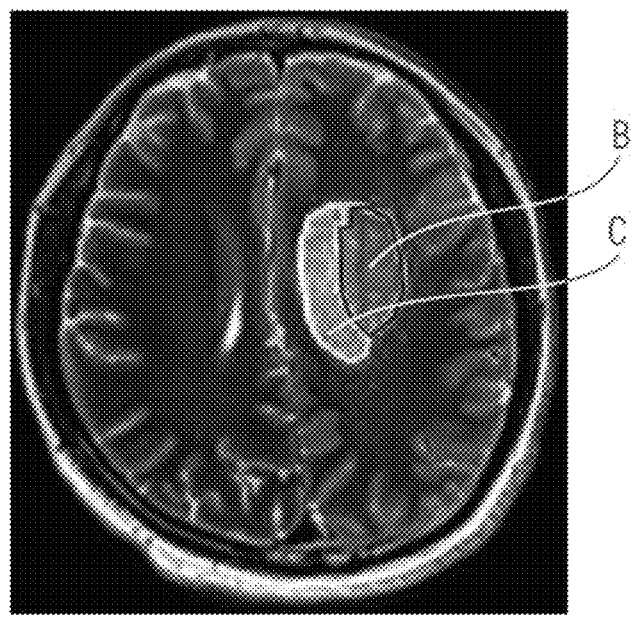
FIG. 2G is a view presented in a standard T2 weighted image after the tumor body region and the edema region are segmented in accordance with the embodiments of the present disclosure.

FIG. 2G is a view presented in a T2 weighted image after the tumor body region and the edema region are segmented in the embodiments of the present disclosure. Wherein, region B is the tumor body region and region C is the edema region.

In addition, the method may further comprise: utilizing a machine learning classification algorithm to classify the signal intensity of the voxel in the same position in the tumor body region in a third set image group according to the predetermined tumor cell grading information (for example, for each voxel in the tumor body region, letting the signal intensity of the voxel in the same position in the third set image group constitute an eigenvector and classifying each eigenvector) to obtain the tumor cell grade of the patient. Wherein, the images included in the third set image group may be determined according to the actual requirements. For example, the third set image group may include any of a patient's low, mid, and high b-value diffusion weighted images, first apparent diffusion coefficient image, and second apparent diffusion coefficient image mentioned in the present application, or any combination thereof, or may include images not mentioned in the present applications. The images included in the third set image group are not restricted here.

Figure 3:
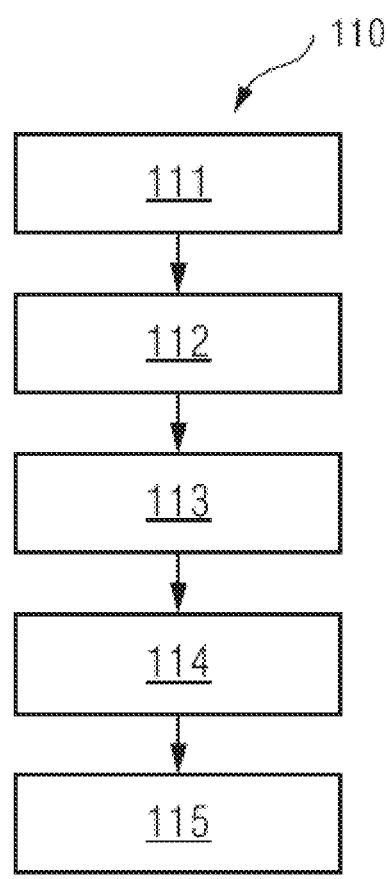
FIG. 3 is a flowchart of a method for realizing step 110 of acquiring a basic white matter template generated based on brain magnetic resonance images of a plurality of healthy samples in the method shown in FIG. 1.

FIG. 3 is a flowchart of a method for realizing step 110 of acquiring a basic white matter template generated based on brain magnetic resonance images of a plurality of healthy samples in the method shown in FIG. 1. As shown in FIG. 4, the method comprises:

Step 111: Collect morphological images of the 3-D standard brain templates of the heads of a plurality of healthy samples and corresponding low, mid, and high b-value diffusion weighted images.

In this step, the morphological images of the 3-D standard brain templates of the heads of the plurality of healthy samples and the corresponding low, mid, and high b-value diffusion weighted images may be obtained by using a magnetic resonance scanner to scan the healthy sample of each volunteer, or may be the images of the healthy samples acquired from the public data of the Human Connectome Project (HCP).

Figure 4A:
FIGS. 4A to 4D are respectively a morphological image of the 3-D standard brain template of a healthy sample, and the corresponding low, mid and high b-value diffusion weighted images in an example embodiment of the present disclosure.
Figure 4B:
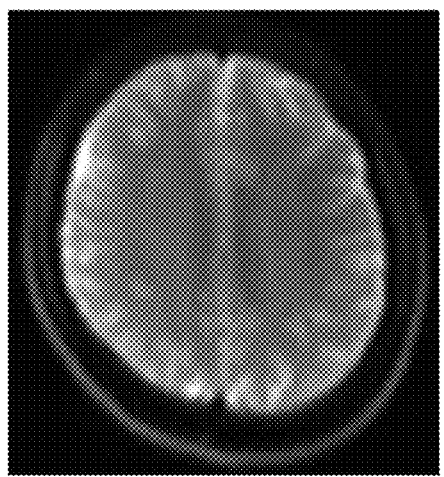
Figure 4C:
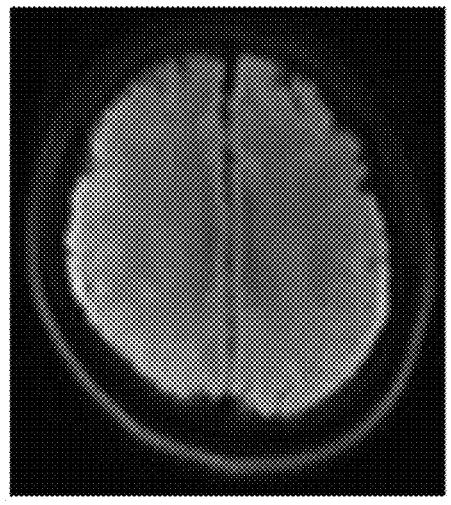
Figure 4D:

FIGS. 4A to 4D are respectively a morphological image of the 3-D standard brain template of a healthy sample, and the corresponding low, mid, and high b-value diffusion weighted images in an example of the present disclosure. Wherein, FIG. 4A is a morphological image of the 3-D standard brain template of the healthy sample, FIG. 4B is a b0 diffusion weighted image of the healthy sample, FIG. 2C is a b1000 diffusion weighted image of the healthy sample, and FIG. 2D is a b10000 diffusion weighted image of the healthy sample.

Step 112: For each healthy sample, register the low, mid, and high b-value diffusion weighted images of the healthy sample with the morphological image of the 3-D standard brain template of the healthy sample to obtain the healthy sample's low, mid, and high b-value diffusion weighted images with the standard space and resolution.

In the embodiments of the present disclosure, the corresponding space and resolution of the morphological image of the 3-D standard brain template are called standard space and resolution.

Step 113: Perform a standard brain template space transformation for the morphological image of the 3-D standard brain template of each healthy sample of the plurality of healthy samples to obtain a transformation matrix of each healthy sample from the individual space to the standard space.

Step 114: For each healthy sample, apply the transformation matrix of the healthy sample to the high b-value diffusion weighted image of the healthy sample in the standard space and resolution condition to obtain the projection of the high b-value diffusion weighted image of each healthy sample in the standard space.

Step 115: Make statistics of the projections of the high b-value diffusion weighted images of the plurality of healthy samples in the standard space to obtain a fiber bundle probability distribution graph of overall samples and use the fiber bundle probability distribution graph as a basic white matter template.

The brain tumor image segmentation method in the embodiments of the present disclosure has been described in detail above, and the brain tumor image segmentation device in the embodiments of the present disclosure will be described in detail below. The brain tumor image segmentation device in the embodiments of the present disclosure may be used to realize the brain tumor image segmentation method in the embodiments of the present disclosure. For the details not disclosed in the embodiments of the brain tumor image segmentation device, refer to the corresponding descriptions in the embodiments of the brain tumor image segmentation method.

Figure 5:
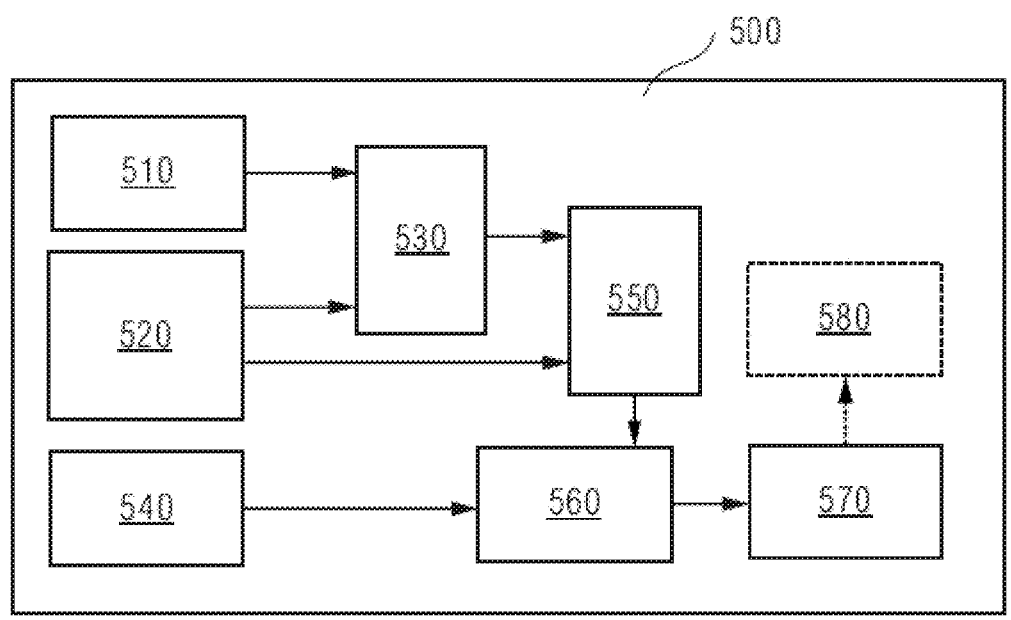
FIG. 5 shows the exemplary structure of one brain tumor image segmentation device in accordance with embodiments of the present disclosure.

FIG. 5 shows the exemplary structure of one brain tumor image segmentation device 500 in the embodiments of the present disclosure. As shown in FIG. 5, the device may comprise: a template generation module 510, an image acquisition module 520, a template transformation module 530, a first region segmentation module 540, a mask generation module 550, a white matter removal module 560, and a second region segmentation module 570, wherein, the template generation module 510 is configured to acquire a basic white matter template generated based on brain magnetic resonance images of a plurality of healthy samples;

the image acquisition module 520 is configured to collect a morphological image of the 3-D standard brain template of the head of a patient and corresponding low, mid, and high b-value diffusion weighted images;

the template transformation module 530 is configured to register the basic white matter template with the morphological image of the 3-D standard brain template of the patient to obtain an individual white matter template, the first region segmentation module 540 is configured to segment out the tumor region including the tumor body and the edema on each image of the patient based on the signal distribution of each image in a first set image group of the patient;

the mask generation module 550 is configured to compare the high b-value diffusion weighted image with the individual white matter template to obtain a mask configured to indicate a normal white matter region;

the white matter removal module 560 is configured to remove the normal white matter region from the tumor region according to the mask, and the second region segmentation region 570 is configured to classify the value of the voxel in each image in a second set image group as an eigenvector for each voxel in the tumor region from which the normal white matter region is removed and segment the image to obtain a tumor body region and an edema region, wherein the second set image group includes the high b-value diffusion weighted image, the first apparent diffusion coefficient image obtained through calculations according to the low and mid b-value diffusion weighted images of the patient and the second apparent diffusion coefficient image obtained through calculations according to the mid and high b-value diffusion weighted images of the patient.

Figure 6:
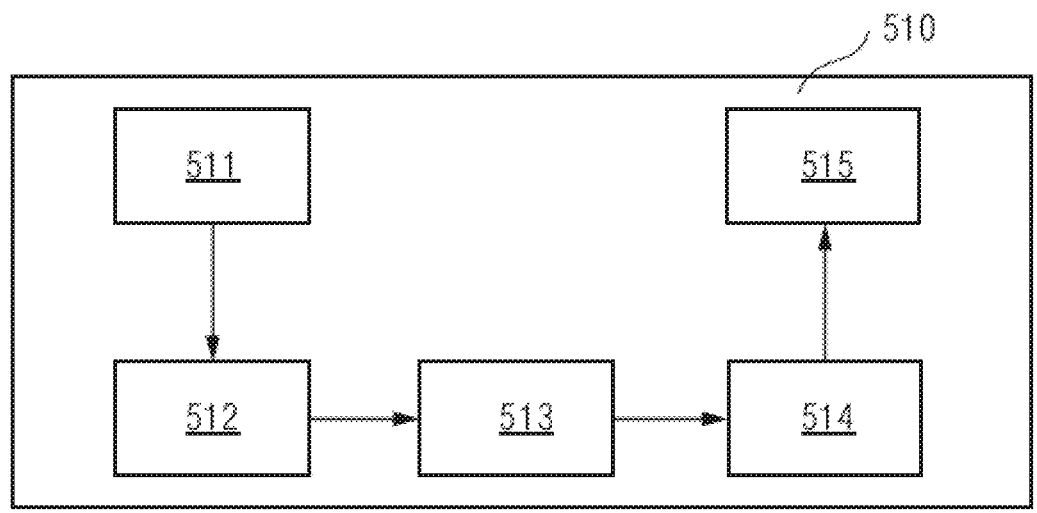
FIG. 6 shows the structure of the template generation module in the device shown in FIG. 5.

In one embodiment, the template generation module 510 may comprise an image acquisition unit 511, a registration unit 512, a space transformation unit 513, a weighted image processing unit 514 and a template determination unit 515, as shown in FIG. 6, wherein, the image acquisition unit 511 is configured to collect morphological images of the 3-D standard brain templates of the heads of a plurality of healthy samples and corresponding low, mid, and high b-value diffusion weighted images;

the registration unit 512 is configured to register the low, mid and high b-value diffusion weighted images of each healthy sample with the morphological image of the 3-D standard brain template of the healthy sample to obtain the healthy sample's low, mid, and high b-value diffusion weighted images with the standard space and resolution;

the space transformation unit 513 is configured to perform a standard brain template space transformation for the morphological image of the 3-D standard brain template of each healthy sample of the plurality of healthy samples to obtain a transformation matrix of each healthy sample from the individual space to the standard space;

the weighted image processing unit 514 is configured to apply the transformation matrix of each healthy sample to the high b-value diffusion weighted image of the healthy sample in the standard space and resolution condition to obtain the projection of the high b-value diffusion weighted image of each healthy sample in the standard space, and the template determination unit 515 is configured to generate statistics of the projections of the high b-value diffusion weighted images of the plurality of healthy samples in the standard space to obtain a fiber bundle probability distribution graph of overall samples and use the fiber bundle probability distribution graph as a basic white matter template.

In one embodiment, the first set image group includes the first apparent diffusion coefficient image and the second apparent diffusion coefficient image; the first region segmentation module 540 segments the first apparent diffusion coefficient image and the second apparent diffusion coefficient image according to the abnormal signal distributions in the two images respectively to obtain the abnormal signal regions and takes the combined set of the two abnormal signal regions to obtain a tumor region including the tumor body and the edema.

In one embodiment, the first set image group includes the low b-value diffusion weighted image, T1 enhanced image, or T2 plain-scan image.

In one embodiment, the device optionally further comprises a grading module 580, configured to classify the eigenvector constituted by the signal intensity of the voxel in the same position in the tumor body region in a third set image group according to the predetermined tumor cell grading information to obtain the tumor cell grade of the patient. In one embodiment, the third set image group includes any of the low, mid, and high b-value diffusion weighted images, the first apparent diffusion coefficient image, and the second apparent diffusion coefficient image of the patient, or any combination thereof.

In one embodiment, the low b-value is a b-value equal to 0, the mid b-value is a b-value ranging from 1000 to 4000, and the high b-value is a b-value greater than 5000.

Figure 7:
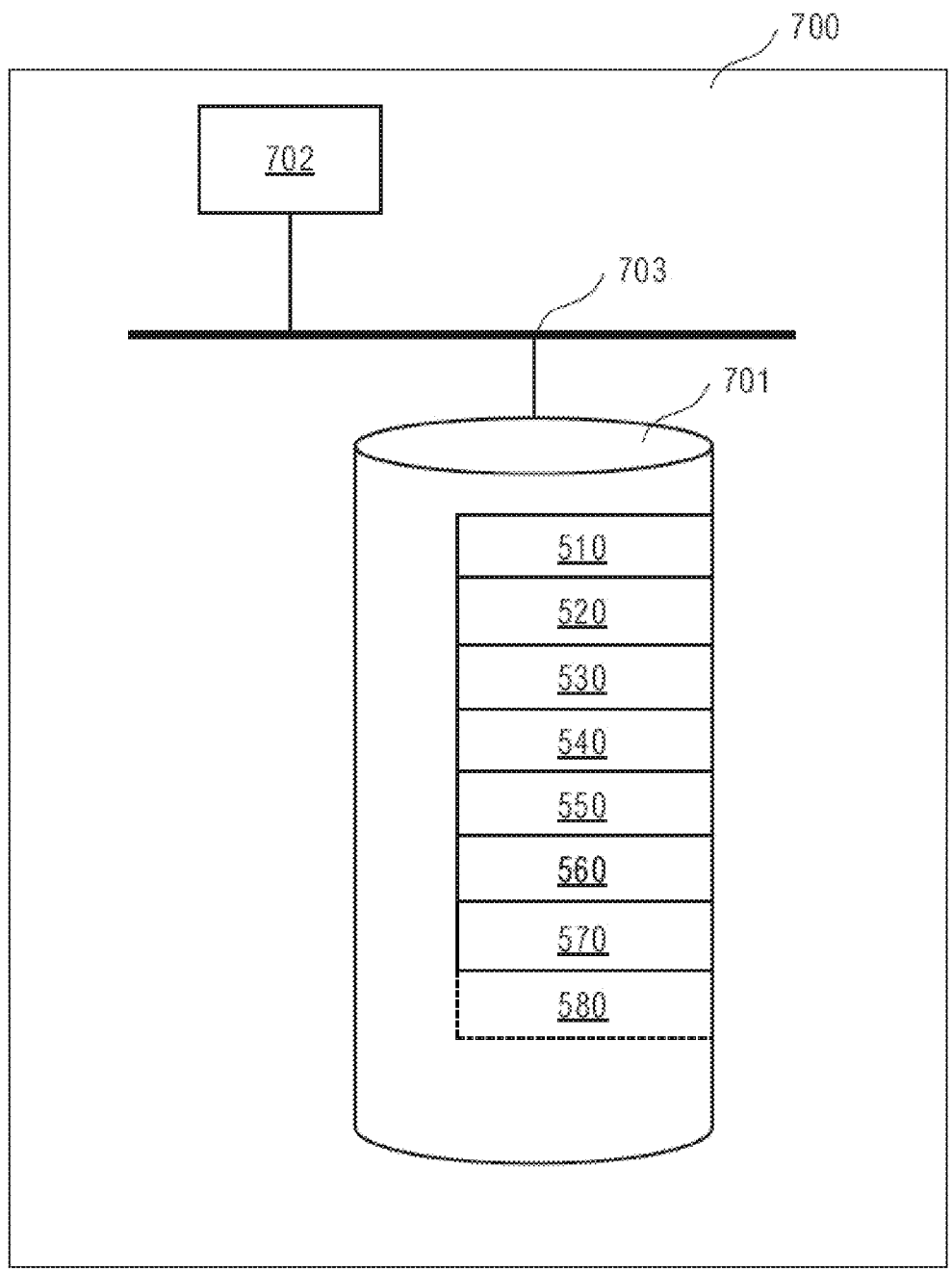
FIG. 7 shows the exemplary structure of another brain tumor image segmentation device in accordance with embodiments of the present disclosure.

FIG. 7 shows the exemplary structure of another brain tumor image segmentation device 700 in the embodiments of the present disclosure. As shown in FIG. 7, the brain tumor image segmentation device 700 may comprise at least a memory 701 and at least a processor 702. Of course, the brain tumor image segmentation device may further comprise some other components, for example, a communication port. These components can communicate with each other through a bus 703.

Wherein, at least one memory 701 is configured to store a computer program. In one embodiment, the computer program may be interpreted as the modules of the brain tumor image segmentation device shown in FIG. 5. For example, the at least one memory 701 may be implemented as a non-transitory computer-readable medium having suitable instructions stored thereon that, when executed by the processor 702 (or another suitable processor not shown in FIG. 7) may facilitate any of the methods as discussed herein.

In addition, at least a memory 701 may further store an operating system. The operating system may include by way of example and not limitation an Android operating system, a Symbian operating system, a Windows operating system, a Linux operating system, etc.

At least the processor 702 may be configured to invoke the computer program stored in at least a memory 701 to execute the brain tumor image segmentation method described in FIG. 1 based on the function of at least a port receiving data. The processor 702 may be a central processing unit (CPU), a processing unit/module, an application specific integrated circuit (ASIC), a logic module, a programmable gate array, etc.

It should be noted that not all the steps or modules in the above-mentioned processes and structural diagrams are required, and some steps or modules can be ignored, depending on the actual requirement and/or application. The execution sequence of the steps is not fixed and may be adjusted as required. The partition of the modules is a functional partition for the convenience of description. In the practical implementation, the function of a module may be realized by a plurality of modules and/or processing circuitry, the functions of a plurality of modules may be realized by one module, and/or these modules may be located in the same equipment or may be located in different equipment.

It should be understood that the hardware modules in different embodiments may be realized mechanically or electronically. For example, a hardware module may comprise specially-designed permanent hardware circuits or logic devices (for example, application-specific processors such as FPGA or ASIC) to complete specific operations. A hardware module may also comprise programmable logic devices or circuits (for example, general processors or other programmable processors) temporarily configured by software to perform specific operations. Whether a hardware module is realized mechanically or by use of a dedicated permanent circuit or a temporarily configured circuit (for example, configured by software) may depend on the considerations such as cost, time, and the particular application.

The present disclosure further provides a machine-readable storage medium (e.g. a non-transitory computer-readable medium), in which commands allowing a machine to execute the method described in the present disclosure are stored. In particular, a system or device equipped with a storage medium may be provided. Software program codes which may realize the function in any of above-mentioned embodiments are stored in the storage medium and the computer (or CPU or MPU) of the system or device may read and execute the program codes stored in the storage medium. In addition, through the commands based on the program codes, the operating system on the computer may complete a part of or all of practical operations. In addition, the program codes read out of the storage medium may be written into the memory in an expansion board in the computer or may be written into the memory in an expansion unit connected to the computer, and then the commands based on the program codes let the CPU installed on the expansion board or expansion unit execute a part or all of practical operations to realize the function in any of the above-mentioned embodiments. The storage medium configured to provide program codes includes a floppy disk, hard disk, magneto-optical disk, optical disk (for example, CD-ROM, CD-R, CD-RW, DVD-ROM, DVD-RAM, DVD-RW, DVD+RW), magnetic tape, non-volatile memory card, ROM, etc. Alternatively, the program codes may be downloaded from the server computer over a communication network.

It can be seen from the above-mentioned solution that high b-value diffusion weighted images which can effectively show a white matter region and apparent diffusion coefficient images which are obtained through calculations based on a set high b-value and a set mid b-value, and can effectively show a gray matter region and a tumor region are introduced in the embodiments of the present disclosure, the white matter region is removed from the tumor region in the above-mentioned two apparent diffusion coefficient images by acquiring the white matter template generated based on the brain magnetic resonance images of healthy samples, and the tumor body region and the edema region are further segmented out by comparing the image of the tumor region from which the white matter region is removed.

In addition, when the tumor region including the tumor body and the edema is segmented, a plurality of optional solutions are available and the segmentation can be realized flexibly.

Further, a method of setting specific low, mid, and high b-values is given.

In addition, the tumor cell grade of a patient is obtained by classifying the eigenvector constituted by the signal intensity of the voxel in the same position in the tumor body region in a third set image group according to the predetermined tumor cell grading information, thus facilitating the subsequent diagnosis and treatment.

The above-mentioned embodiments are preferred embodiments of the present disclosure provide by way of example, and should not be interpreted as restricting the present disclosure to these specific examples. Without departing the spirit and principle of the present disclosure, modifications, equivalent replacements, and improvements all fall within the scope of protection of the present disclosure.

What is claimed is:

1. A brain tumor image segmentation method used as part of a magnetic resonance imaging system, the method comprising:

acquiring a basic white matter template that is generated based on brain magnetic resonance images of a plurality of healthy samples;

collecting a morphological image of a 3-D standard brain template of the head of a patient and corresponding low, mid, and high b-value diffusion weighted images;

registering the basic white matter template with the morphological image of the 3-D standard brain template to obtain an individual white matter template;

comparing the high b-value diffusion weighted image corresponding to the morphological image of the 3-D standard brain template of the head of the patient with the individual white matter template to obtain a mask that indicates a normal white matter region in the patient;

removing the normal white matter region from a tumor region according to the mask;

for each image of the patient from among a plurality of patient images, segmenting out the tumor region, which includes the a tumor body region and an edema region, based on a signal distribution associated with each of the plurality of patient images included as part of a first image set; and for each voxel in the segmenting tumor region from which the normal white matter region is removed, (i) classifying the value of each voxel in each of the plurality of patient images within a second image set as an eigenvector, and (ii) segmenting the plurality of patient images within the second image set to obtain the tumor body region and the edema region, wherein the second image set includes (i) the high b-value diffusion weighted image, (ii) a first apparent diffusion coefficient image obtained via calculations according to the low b-value diffusion weighted images of the patient and the mid b-value diffusion weighted images of the patient, and (iii) a second apparent diffusion coefficient image obtained via calculations according to the mid b-value diffusion weighted images of the patient and the high b-value diffusion weighted images of the patient.

2. The method as claimed in claim 1, wherein the act of acquiring the basic white matter template generated comprises:

collecting morphological images of the 3-D standard brain templates of the heads of a plurality of healthy samples and corresponding low, mid, and high b-value diffusion weighted images;

for each of the plurality of healthy samples, registering the low, mid, and high b-value diffusion weighted images of the healthy sample with the morphological image of the 3-D standard brain template of the healthy sample to obtain the healthy sample's low, mid, and high b-value diffusion weighted images having a standard space and resolution;

performing a standard brain template space transformation for the morphological image of the 3-D standard brain template of each healthy sample of the plurality of healthy samples to obtain a transformation matrix of each healthy sample from an individual space to the standard space;

for each healthy sample, applying the transformation matrix of the healthy sample to the high b-value diffusion weighted image of the healthy sample in the standard space and resolution to obtain a projection of the high b-value diffusion weighted image of each healthy sample in the standard space;

calculating statistics of the projections of the high b-value diffusion weighted images of the plurality of healthy samples in the standard space to obtain a fiber bundle probability distribution graph of overall samples; and using the fiber bundle probability distribution graph as the basic white matter template.

3. The method as claimed in claim 1, wherein the first image set of the plurality of patient images includes the first apparent diffusion coefficient image and the second apparent diffusion coefficient image, and wherein the act of segmenting out the tumor region including the tumor body region and the edema region for each image of the patient from among the plurality of patient images comprises:

segmenting the first apparent diffusion coefficient image and the second apparent diffusion coefficient image according to abnormal signal distributions in the first apparent diffusion coefficient image and the second apparent diffusion coefficient image, respectively, to obtain two abnormal signal regions; and calculating a union set of the two abnormal signal regions to obtain a tumor region including the tumor body region and the edema region.

4. The method as claimed in claim 1, wherein the first image set of the plurality of patient images includes the low b-value diffusion weighted image, a T1 enhanced image, or a T2 plain-scan image.

5. The method as claimed in claim 1, further comprising:

classifying the eigenvector constituted by the signal intensity of the voxel in the same position in the tumor body region in a third image set of the plurality of the patient images according to a predetermined tumor cell grading information to obtain a tumor cell grade of the patient.

6. The method as claimed in claim 5, wherein the third image set of the plurality of the patient images includes one or more of the low, mid, and high b-value diffusion weighted images, the first apparent diffusion coefficient image, and the second apparent diffusion coefficient image of the patient.

7. The method as claimed in claim 1, wherein the low b-value is a b-value equal to 0, the mid b-value is a b-value ranging from 1000 to 4000, and the high b-value is a b-value greater than 5000.

8. A brain tumor image segmentation device used as part of a magnetic resonance imaging system, the device comprising:

a template generation module configured to acquire a basic white matter template that is generated based on brain magnetic resonance images of a plurality of healthy samples;

an image acquisition module configured to collect a morphological image of a 3-D standard brain template of the head of a patient and corresponding low, mid, and high b-value diffusion weighted images;

a template transformation module configured to register the basic white matter template with the morphological image of the 3-D standard brain template to obtain an individual white matter template;

a mask generation module configured to compare the high b-value diffusion weighted image corresponding to the morphological image of the 3-D standard brain template of the head of the patient with the individual white matter template to obtain a mask used to indicate a normal white matter region in the patient;

a white matter removal module configured to remove the normal white matter region from a tumor region according to the mask;

a first region segmentation module configured to, for each image of the patient from among a plurality of patient images, segment out the tumor region, which includes a tumor body region and an edema region, based on a signal distribution associated with each of the plurality of patient images included as part of a first image set; and a second region segmentation module configured to, for each voxel in the segmenting tumor region from which the normal white matter region is removed, (i) classify the value of each voxel in each of the plurality of patient images within a second image set as an eigenvector, and (ii) segment the plurality of patient images within the second image set to obtain the tumor body region and the edema region, wherein the second image set includes (i) the high b-value diffusion weighted image, (ii) a first apparent diffusion coefficient image obtained via calculations according to the low and mid b-value diffusion weighted images of the patient, and (iii) a second apparent diffusion coefficient image.

9. The device as claimed in claim 8, wherein the template generation module comprises:

an image acquisition unit configured to collect morphological images of the 3-D standard brain templates of the heads of a plurality of healthy samples and corresponding low, mid, and high b-value diffusion weighted images;

a registration unit configured to register, of the plurality of healthy samples, the low, mid, and high b-value diffusion weighted images of each healthy sample with the morphological image of the 3-D standard brain template of the healthy sample to obtain the healthy sample's low, mid, and high b-value diffusion weighted images having a standard space and resolution;

a space transformation unit configured to perform a standard brain template space transformation for the morphological image of the 3-D standard brain template of each healthy sample of the plurality of healthy samples to obtain a transformation matrix of each healthy sample from an individual space to the standard space;

a weighted image processing unit configured to apply the transformation matrix of each healthy sample to the high b-value diffusion weighted image of the healthy sample in the standard space and resolution to obtain a projection of the high b-value diffusion weighted image of each healthy sample in the standard space;

a template determination unit configured to calculate statistics of the projections of the high b-value diffusion weighted images of the plurality of healthy samples in the standard space to obtain a fiber bundle probability distribution graph of overall samples, and to use the fiber bundle probability distribution graph as the basic white matter template.

10. The device as claimed in claim 8, wherein the first image set of the plurality of patient images includes the first apparent diffusion coefficient image and the second apparent diffusion coefficient image, and wherein the first region segmentation module is further configured to segment the first apparent diffusion coefficient image and the second apparent diffusion coefficient image according to abnormal signal distributions in the first apparent diffusion coefficient image and the second apparent diffusion coefficient image, respectively, to obtain two abnormal signal regions, and calculate a union set of the two abnormal signal regions to obtain a tumor region including the tumor body and the edema region.

11. The device as claimed in claim 8, wherein the first image set of the plurality of patient images includes the low b-value diffusion weighted image, a T1 enhanced image, or a T2 plain-scan image.

12. The device as claimed in claim 8, the device further comprising:

a grading module configured to classify the eigenvector constituted by the signal intensity of the voxel in the same position in the tumor body region in a third image set of the plurality of the patient images according to a predetermined tumor cell grading information to obtain a tumor cell grade of the patient.

13. The device as claimed in claim 12, wherein the third image set of the plurality of the patient images includes one or more of the low, mid, and high b-value diffusion weighted images, the first apparent diffusion coefficient image, and the second apparent diffusion coefficient image of the patient.

14. The device as claimed in claim 8, wherein the low b-value is a b-value equal to 0, the mid b-value is a b-value ranging from 1000 to 4000, and the high b-value is a b-value greater than 5000.

15. A non-transitory computer-readable medium of a brain tumor image segmentation device used as part of a magnetic resonance imaging system, the non-transitory computer-readable having instructions stored thereon that, when executed by one or more processors of the magnetic resonance imaging system, causes the magnetic resonance imaging system to:

acquire a basic white matter template that is generated based on brain magnetic resonance images of a plurality of healthy samples;

collect a morphological image of a 3-D standard brain template of the head of a patient and corresponding low, mid, and high b-value diffusion weighted images;

register the basic white matter template with the morphological image of the 3-D standard brain template to obtain an individual white matter template;

compare the high b-value diffusion weighted image corresponding to the morphological image of the 3-D standard brain template of the head of the patient with the individual white matter template to obtain a mask used to indicate a normal white matter region in the patient;

remove the normal white matter region from a tumor region according to the mask;

for each image of the patient from among a plurality of patient images, segment out the tumor region, which includes a tumor body region and an edema region, based on a signal distribution associated with each of the plurality of patient images included as part of a first image set; and for each voxel in the segmenting tumor region from which the normal white matter region is removed, (i) classify the value of each voxel in each of the plurality of patient images within a second image set as an eigenvector, and (ii) segment the plurality of patient images within the second image set to obtain the tumor body region and the edema region, wherein the second image set includes (i) the high b-value diffusion weighted image, (ii) a first apparent diffusion coefficient image obtained via calculations according to the low and mid b-value diffusion weighted images of the patient, and (iii) a second apparent diffusion coefficient image.

* * * * *